United States Patent
Avila et al.

[11] Patent Number: 5,934,288
[45] Date of Patent: Aug. 10, 1999

[54] METHOD AND APPARATUS FOR DISPLAYING 3D ULTRASOUND DATA USING THREE MODES OF OPERATION

[75] Inventors: Ricardo Scott Avila; Lisa Sobierajski Avila, both of Clifton Park, N.Y.; Brian Peter Geiser, Pewaukee, Wis.; William Thomas Hatfield, Schenectady, N.Y.; Todd Michael Tillman, West Milkauwee, Wis.

[73] Assignee: General Electric Company, Schenectady, N.Y.

[21] Appl. No.: 09/065,211

[22] Filed: Apr. 23, 1998

[51] Int. Cl.⁶ ........................................ A61B 8/00
[52] U.S. Cl. ............................................. 128/916
[58] Field of Search ............... 128/916; 600/443; 340/988, 990, 995; 395/124; 345/425, 426

[56] References Cited

U.S. PATENT DOCUMENTS

| | | | |
|---|---|---|---|
| 5,538,004 | 7/1996 | Bamber | 128/916 |
| 5,644,689 | 7/1997 | Ban et al. | 395/124 |
| 5,782,766 | 7/1998 | Weng et al. | 128/916 |
| 5,787,889 | 8/1998 | Edwards et al. | 128/916 |
| 5,817,022 | 10/1998 | Vesely et al. | 128/916 |

*Primary Examiner*—Marvin M. Lateef
*Assistant Examiner*—Ali M. Imam
*Attorney, Agent, or Firm*—Marvin Snyder; Douglas E. Stoner

[57] ABSTRACT

A method and an apparatus for allowing the operator of an ultrasound imaging system to switch between two-dimensional slices and three-dimensional projections in such a way that it is easy for the operator to visualize the relationship of the two-dimensional slice to the three-dimensional anatomy. In a "volume rotate" mode, the display screen displays an orientation box along with a three-dimensional projected image generated from a defined data volume. The orientation box provides a visual indication of the shape and orientation of that defined data volume. In a "cut plane" mode, a movable polygon representing a selected two-dimensional slice is displayed inside a stationary orientation box. The polygon provides a visual indication of the orientation and position of the slice relative to the defined data volume. In a "cut plane rotate" mode, a stationary polygon representing a selected two-dimensional slice is displayed inside a rotatable orientation box.

20 Claims, 8 Drawing Sheets

METHOD AND APPARATUS FOR DISPLAYING 3D ULTRASOUND DATA USING THREE MODES OF OPERATION

FIELD OF THE INVENTION

This invention generally relates to three-dimensional ultrasound imaging of the human anatomy for the purpose of medical diagnosis. In particular, the invention relates to methods and apparatus for three-dimensional imaging of the human anatomy by detecting the ultrasonic echoes reflected from a scanned volume in a human body.

BACKGROUND OF THE INVENTION

Conventional ultrasound scanners create two-dimensional B-mode images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. In power Doppler imaging, the power contained in the returned Doppler signal is displayed. Although the following disclosure refers predominantly to B-mode imaging for the sake of brevity, the present invention applies to any mode of ultrasound imaging.

Figure 1:
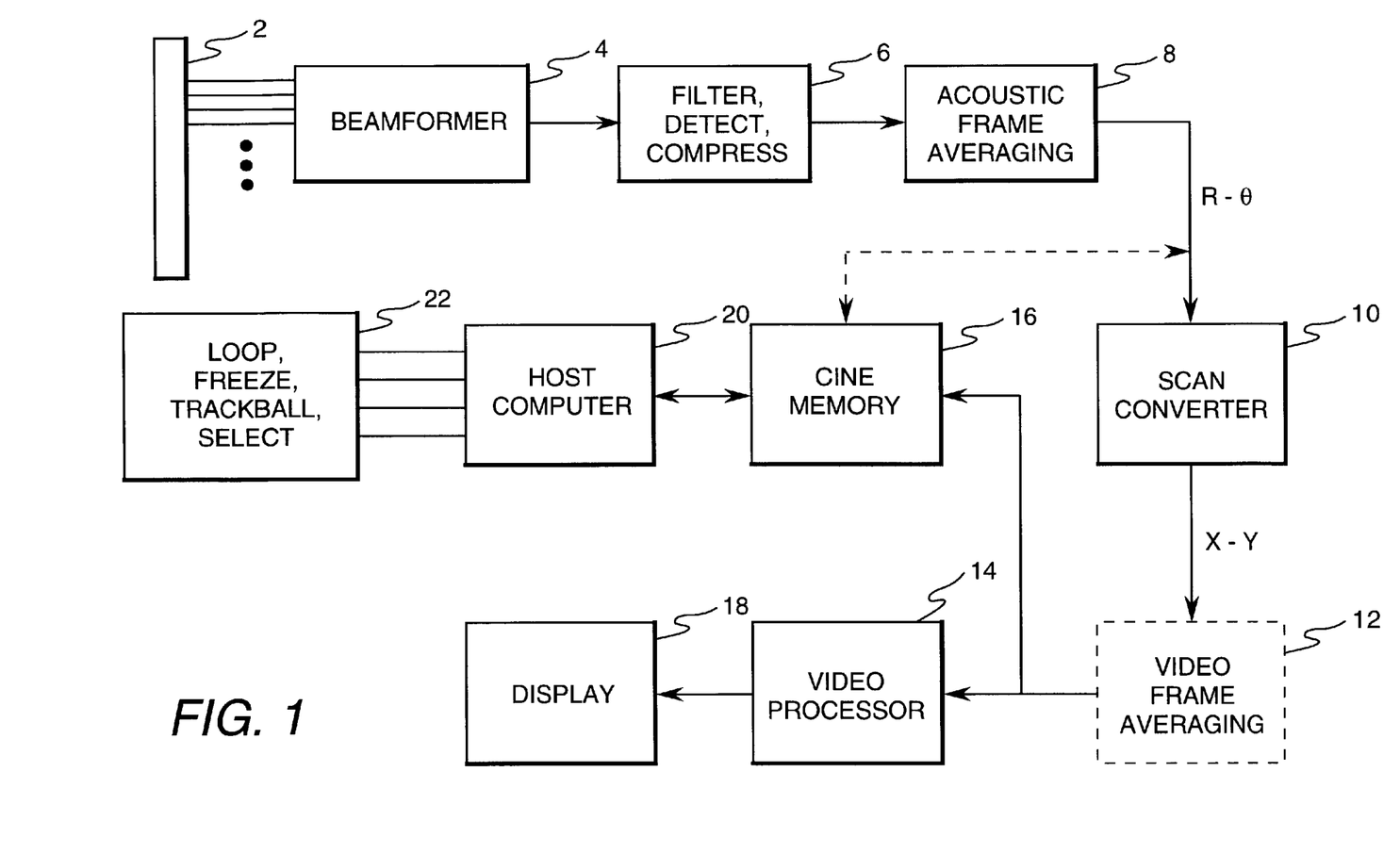
FIG. 1 is a block diagram showing the major functional subsystems within a real-time ultrasound imaging system.

The basic signal processing chain in the conventional B mode is depicted in FIG. 1. An ultrasound transducer array 2 is activated to transmit an acoustic burst along a scan line. The return RF signals are detected by the transducer elements and then formed into a receive beam by the beamformer 4. The beamformer output data (I/Q or RF) for each scan line is passed through a B-mode processing chain 6 which includes equalization filtering, envelope detection and logarithmic compression. Depending on the scan geometry, up to a few hundred vectors may be used to form a single acoustic image frame. To smooth the temporal transition from one acoustic frame to the next, some acoustic frame averaging 8 may be performed before scan conversion. For a sector scan, compressed images in R-θ format are converted by the scan converter 10 into X-Y format for display. On some systems, frame averaging may be performed on the X-Y data (indicated by dashed block 12) rather than the acoustic frames before scan conversion, and sometimes duplicate video frames may be inserted between acoustic frames in order to achieve a given video display frame rate (typically 30 Hz). The scan-converted frames are passed on to a video processor 14, which basically maps the scan-converted data to a display gray or color map for video display.

System control is centered in a host computer 20, which accepts operator inputs through an operator interface 22 (e.g., keyboard and track-ball) and in turn controls the various subsystems. (In FIG. 1, the system control lines from the host computer to the various subsystems have been omitted for the sake of simplicity.) During imaging, a long sequence of the most recent images are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed on the display monitor via track-ball control (interface 22), and a section of the image loop can be selected for hard disk storage. For an ultrasound scanner with free-hand three-dimensional imaging capability, the selected image sequence stored in cine memory 16 is transferred to the host computer 20 for three-dimensional reconstruction. The result is written back into another portion of the cine memory or to scan converter memory, from where it is sent to the display system 18 via video processor 14.

Figure 2:
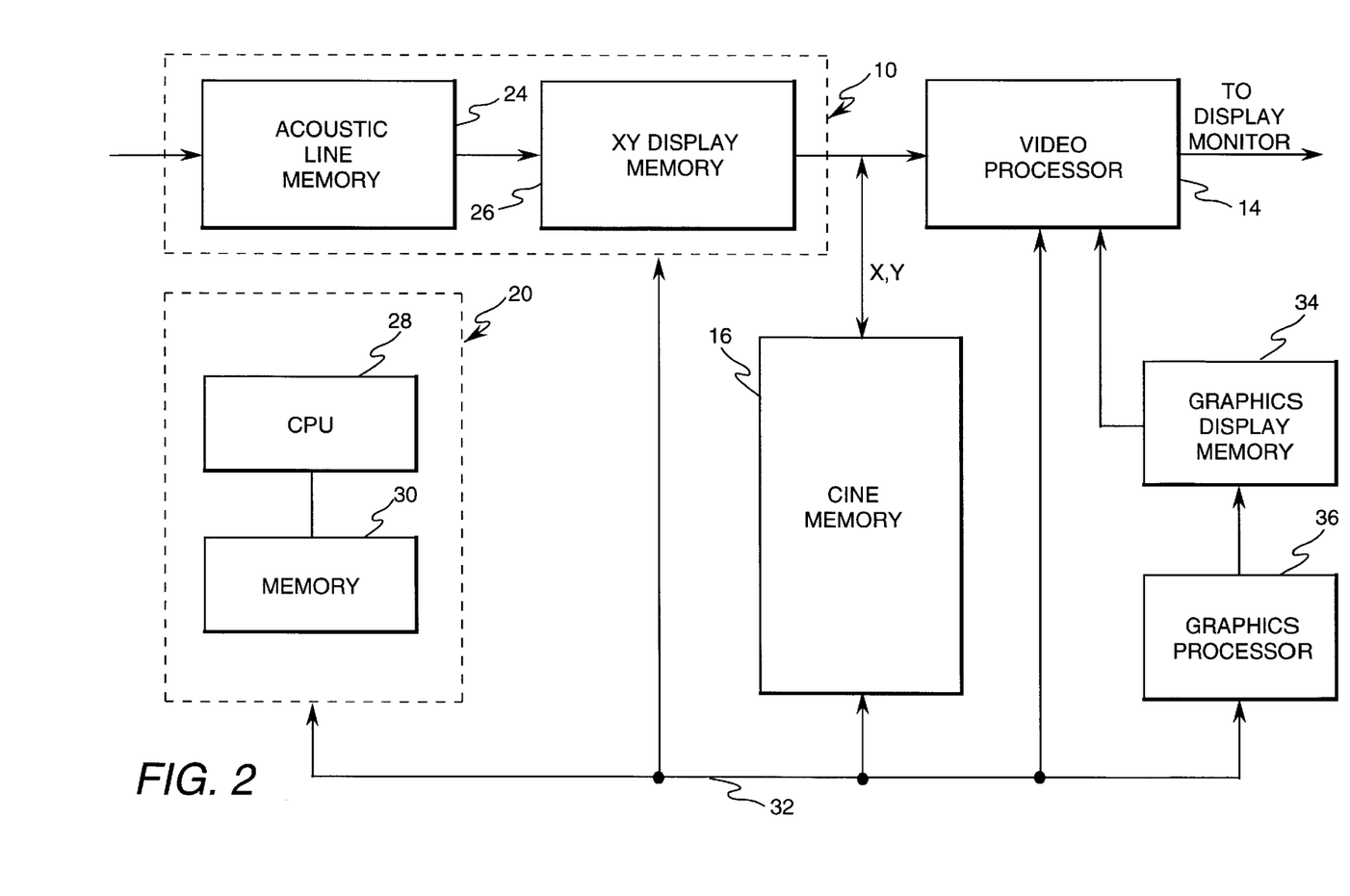
FIG. 2 is a block diagram showing means for reconstructing frames comprising successive volumetric projections of pixel intensity data.

Referring to FIG. 2, the scan converter 10 comprises an acoustic line memory 24 and an XY display memory 26. [A separate acoustic line memory (not shown) is provided for color flow acoustic samples.] The B-mode data stored in polar coordinate (R-θ) sector format in acoustic line memory 24 is transformed to appropriately scaled Cartesian coordinate intensity data, which is stored in XY display memory 26. Each image frame out of XY display memory 26 is sent to both the video processor 14 and the cine memory 16.

A multiplicity of successive frames of B-mode data are stored in cine memory 16 on a first-in, first-out basis. The cine memory is like a circular image buffer that runs in the background, continually capturing image data that is displayed in real time to the user. When the user freezes the system (by depressing the FREEZE key on the interface 22), the user has the capability to view image data previously captured in cine memory.

The conventional system has the capability to superimpose graphical symbols on any ultrasound image. The superimposition of graphics on the image frame is accomplished in the video processor 14, which receives the ultrasound image frame from the XY display memory 26 and the graphics data from a graphics display memory 34. The graphics data is processed and input into the graphics display memory 34 by a graphics processor 36, which is synchronized with the other subsystems by the host computer 20.

The host computer 20 comprises a central processing unit (CPU) 28 and a random access memory 30. The CPU 28 has memory for storing routines used in transforming an acquired volume of intensity data into a multiplicity of three-dimensional projection images taken at different angles. The CPU 28 controls the X-Y memory 26 and the cine memory 16 via the system control bus 32. In particular, the CPU 28 controls the flow of data from the acoustic line memory 24 or from the X-Y memory 26 of the scan converter 10 to the video processor 14 and to the cine memory 16, and from the cine memory to the video processor 14 and to the CPU 28 itself. Each frame of imaging data, representing one of a multiplicity of scans or slices through the object being examined, is stored sequentially in the acoustic line memory 24, in the X-Y memory 26 and in the video processor 14. In parallel, image frames from either the acoustic line memory or the X-Y memory are stored in cine memory 16. A stack of frames, representing the scanned object volume, is stored in cine memory 16, forming a data volume.

Two-dimensional ultrasound images are often hard to interpret due to the inability of the observer to visualize the two-dimensional representation of the anatomy being scanned. However, if the ultrasound probe is swept over an area of interest and two-dimensional images are accumulated to form a three-dimensional data volume, the anatomy becomes much easier to visualize for both the trained and untrained observer.

In order to generate three-dimensional images, the CPU 28 can transform a source data volume retrieved from cine memory 16 into an imaging plane data set. The successive transformations may involve a variety of projection techniques such as maximum, minimum, composite, surface or averaged projections made at angular increments, e.g., at 100 intervals, within a range of angles, e.g., +90° to −90°. Each pixel in the projected image includes the transformed data derived by projection onto a given image plane.

In free-hand three-dimensional ultrasound scans, a transducer array (1 D to 1.5 D) is translated in the elevation direction to acquire a substantially parallel set of image planes through the anatomy of interest. These images can be stored in the cine memory and later retrieved by the system computer for three-dimensional reconstruction. If the spacings between image frames are known, then the three-dimensional volume can be reconstructed with the correct aspect ratio between the out-of-plane and scan plane dimensions. If, however, the estimates of the interslice spacing are poor, significant geometric distortion of the three-dimensional object can result.

A conventional ultrasound scanner collects B-mode, color and power Doppler data in a cine memory on a continuous basis. As the probe is swept over an area of the anatomy, using either a free-hand scanning technique or a mechanical probe mover of some sort, a three-dimensional volume is stored in the cine memory. The distance the probe was translated may be determined by a number of techniques. The user can provide an estimate of the distance swept. If the probe is moved at a constant rate by a probe mover, the distance can easily be determined. Alternatively, a position sensor can be attached to the probe to determine the position of each slice. Markers on the anatomy or within the data could also provide the required position information. Yet another way would be to estimate the scan plane displacements directly from the degree of speckle decorrelation between successive image frames. Once the data volume has been acquired, the central processing unit can then provide three-dimensional projections of the data as well as arbitrary slices through the data volume.

Figure 3:
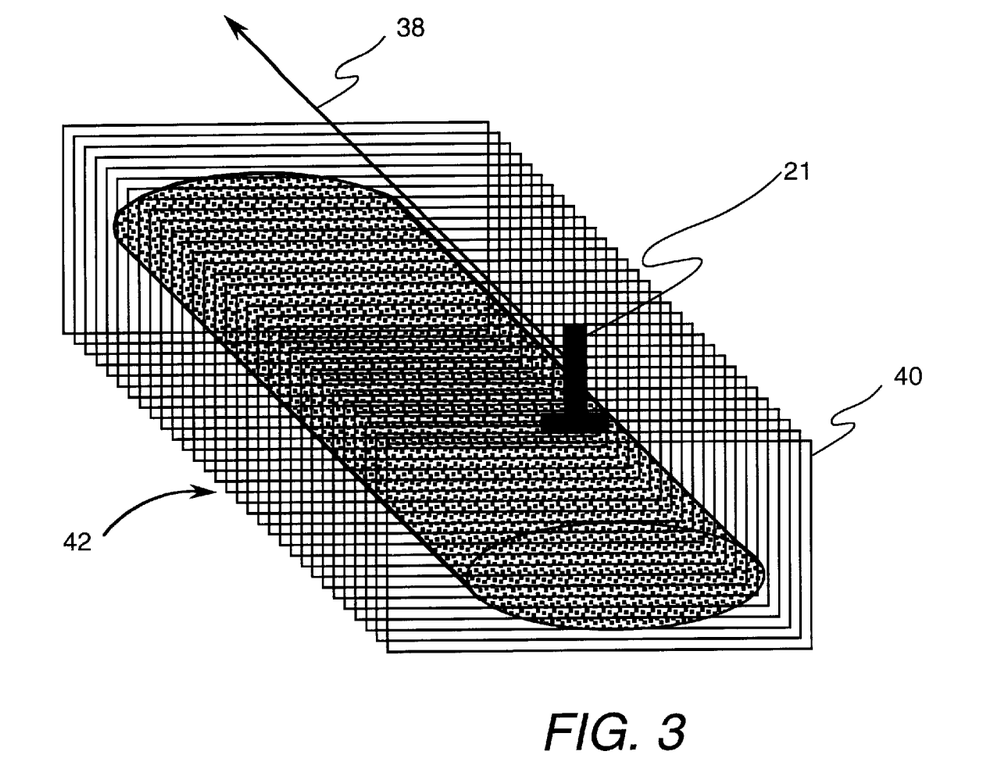
FIG. 3 is a diagram depicting a volume of data acquired by linearly scanning an ultrasound probe in a direction perpendicular to the scan plane of the probe.
Figure 4:
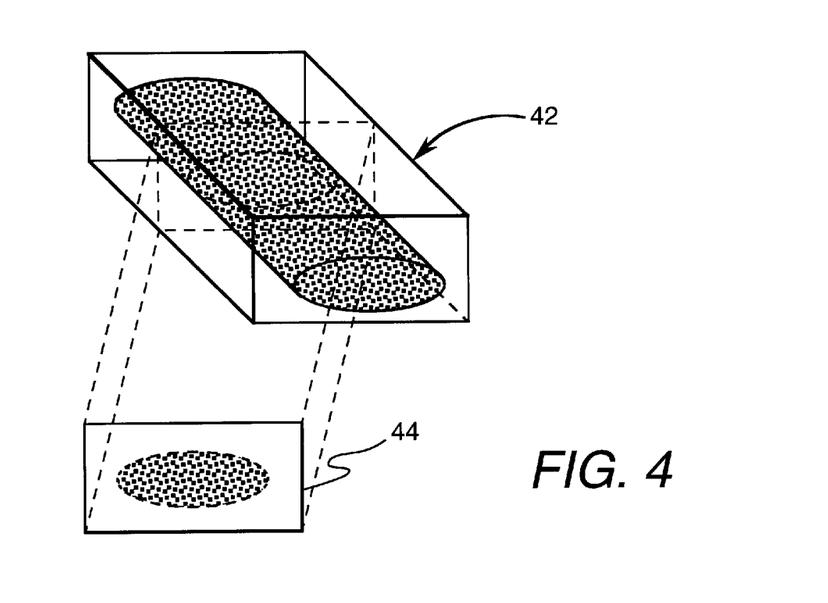
FIG. 4 is a diagram depicting an individual slice at an arbitrary angle obtained by reformatting the data volume depicted in FIG. 3.

Referring to FIG. 3, if the ultrasound probe 2' is swept (arrow 38 indicates a linear sweep) over an area of a body (either by hand or by a probe mover), such that the interslice spacing is known, and the slices 40 are stored in memory, a three-dimensional data volume 42 can be acquired. The data volume can be processed (e.g., using projection onto an imaging plane) to form a three-dimensional view of the area of interest. In addition, the data can be reformatted to produce an individual slice 44 at an arbitrary angle (see FIG. 4), thus allowing the user to get the exact view desired regardless of the anatomy under investigation. Algorithms for producing three-dimensional projections of two-dimensional data are well known, as are techniques for reformatting data to produce arbitrary slices through a data set. The problem that arises is how to display the information such that it is easy for the observer to easily relate the two-dimensional slice to the three-dimensional anatomy.

SUMMARY OF THE INVENTION

The present invention incorporates a user interface designed to allow the operator of an ultrasound imaging system to switch between two-dimensional slices and three-dimensional projections in such a way that it is easy for the operator to visualize the relationship of the two-dimensional slice to the three-dimensional anatomy.

In accordance with a preferred embodiment of the invention, in a "volume rotate" mode, the display screen displays an orientation box along with a three-dimensional projected image generated from a defined data volume. The orientation box provides a visual indication of the shape and orientation of that defined data volume.

Although the orientation box can be used in conjunction with any known technique for projecting three-dimensional images from a data volume at arbitrary angles, in accordance with a preferred technique, voxel data is multiplied by aspect scaling factors, rotated by the desired angle and projected onto an image plane. In accordance with a further aspect of the preferred projection technique, scaling factors are used to ensure that voxels which are one unit apart along the X, Y and Z axes in data space are mapped onto pixels that are at most one unit apart along the X and Y axes on the image plane.

In a "cut plane" mode, a movable polygon representing a selected two-dimensional slice is displayed inside a stationary orientation box. The polygon provides a visual indication of the orientation and position of the slice relative to the defined data volume. The operator may use a track-ball to scroll through the data volume in order to display a desired two-dimensional slice. The polygon is moved inside the orientation box as a function of the track-ball movement to indicate the position of a two-dimensional slice relative to the defined data volume. When the track-ball is stopped, the position of the polygon relative to the orientation box is frozen and the reformatted slice having a corresponding position relative to the defined data volume is displayed.

In a "cut plane rotate" mode, a stationary polygon representing a selected two-dimensional slice is displayed inside a rotatable orientation box. The operator moves a track-ball to rotate the orientation box. The shape of the polygon changes to conform to the changing shape of the two-dimensional slice. When the track-ball is stopped, the orientation of the orientation box relative to the polygon is frozen and the reformatted slice having a position corresponding to the position of the polygon is displayed.

DETAILED DESCRIPTION OF THE PREFERRED EMBODIMENTS

Figure 5:
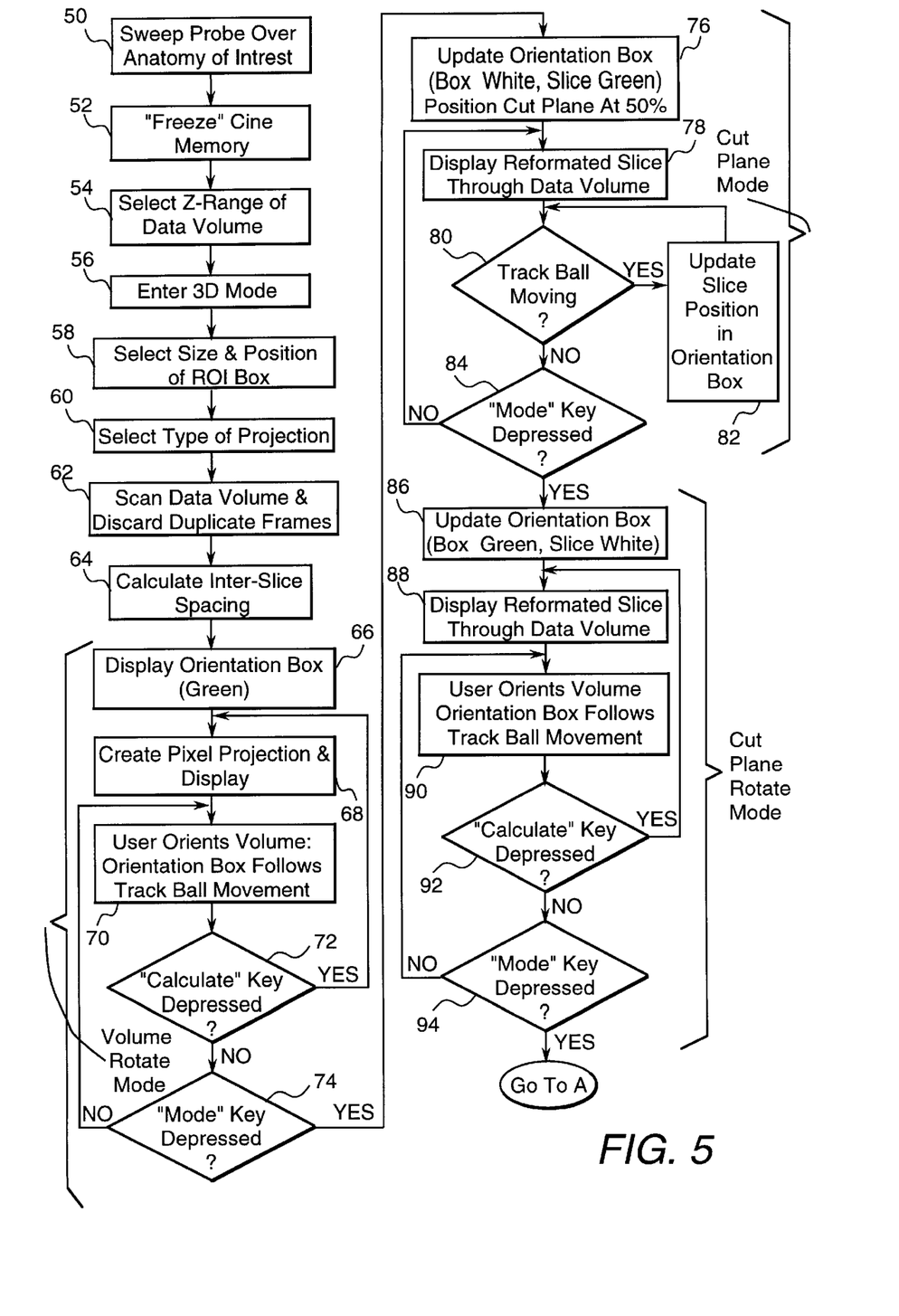
FIG. 5 is a flow chart showing an acquisition and display procedure in accordance with a preferred embodiment of the invention.
Figure 6:
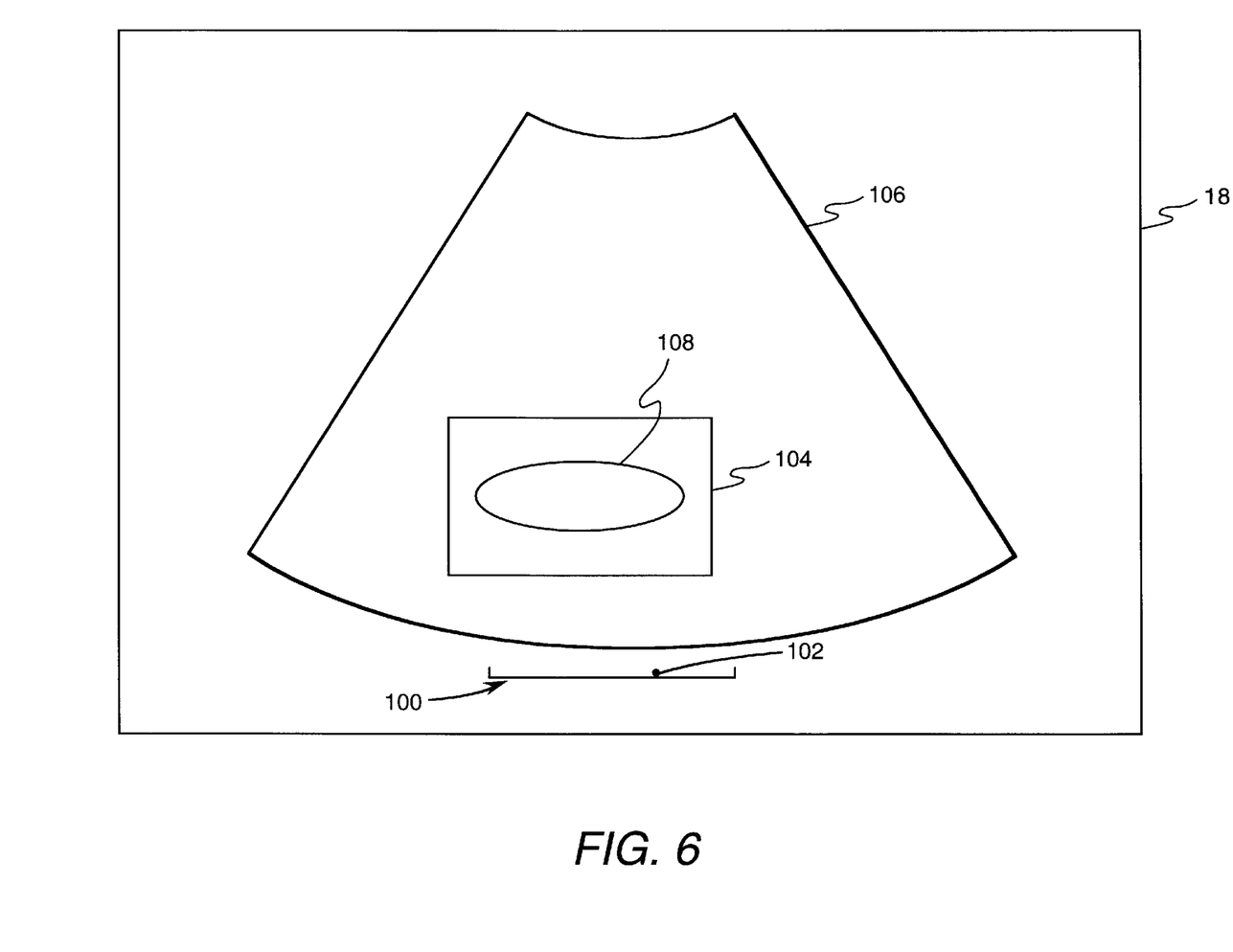
FIG. 6 is a diagram depicting a display of a sector scan ultrasound image with graphics indicating a user-defined volume of interest.

FIG. 5 shows a flow chart of the acquisition and display procedure. The user begins by sweeping the ultrasound probe over an area of interest (step 50). For example, the sweep may be acquired by a free-hand sweep in a linear or rocking motion. Once the data is acquired, the user "freezes" the cine memory (step 52) by depressing the FREEZE key and then selects the range of cine memory frames (slices) to be included in the Z-dimension of the data volume (step 54). The operator accomplishes the latter step by moving a track-ball. As seen in FIG. 6, a Z-dimension select gauge 100 appears on the display screen 18' when the track-ball is moved. The track-ball is then used to control the position of an indicator 102 relative to the gauge 100. The indicator can be moved to a desired left end point and then the left end point is locked by depression of predetermined key on the operator interface. Then the indicator can be moved to a desired right end point and then the right end point is locked by depression of the same predetermined key. This establishes the slices to be included in the data volume. The operator then enters the particular "3D mode" desired, i.e., the "re-slice" mode, by depressing the appropriate key on the interface (step 56).

Upon entering the re-slice mode, the operator must first select the XY-dimension and location of the data volume (step 58). This step is accomplished by manipulating a region of interest box 104 (shown in FIG. 6) which appears in a default position on the display screen 18' in response to depression of the re-slice mode key. The region of interest box 104 can be sized and translated in X and Y to encompass an imaged structure 108 which appears on the sector scan image 106. The region of interest box 104 is translated by moving the track-ball and is sized by operation of a four-sided rocker switch incorporated in the operator interface. For example, the rocker switch is programmed so that the region of interest increases in size in the Y dimension when the switch is moved downward; decreases in size in the Y dimension when the switch is moved upward; increases in size in the X dimension when the switch is moved rightward; and decreases in size in the X dimension when the switch is moved leftward.

After the data volume has been defined, the operator selects (step 60 in FIG. 5) the type of three-dimensional projection desired (minimum or maximum pixel projection, surface, composite, etc.) and presses a render key. The defined data volume is then retrieved from cine memory 16 (see FIG. 2) by the host computer 20. The host computer scans the retrieved data for duplicate frames and discards them (step 62). The host computer then calculates the inter-slice spacing for the data set (step 64). (The inter-slice spacing is assumed to be constant over the length of the data volume.) For example, the inter-slice spacing can be calculated using the adaptive speckle correlation technique disclosed in U.S. patent application Ser. No. 09/045,780 filed on Mar. 20, 1998, the disclosure of which is incorporated by reference herein.

After the inter-slice spacing has been calculated, the system enters a "volume rotate" mode, which is one of three sub-modes included in the so-called "re-slice" mode. Referring to FIG. 2, in the "volume rotate" mode, signals representing a colored (e.g., green) orientation box are generated by the graphics processor 36, arranged in XY format in the graphics display memory 34 and then sent to the video processor 14. The video processor causes a green orientation box to be displayed on display screen (step 66). At the same time the host computer performs the selected projection of the defined data volume based on the calculated inter-slice spacing (step 68). The projected three-dimensional image is sent to the XY display memory 26 and then on to the video processor 14. The projected three-dimensional image is also captured by the cine memory 16. The video processor 14 causes the projected three-dimensional image to be displayed on display screen along with the orientation box. Both the orientation box and the initial projection are oriented with the Z axis pointing into the screen, the Y axis vertical, and the X axis horizontal, i.e., the orientation box appears as a rectangle having X and Y dimensions proportional to the X and Y dimensions of the selected region of interest. The data slices are acquired along the Z axis. This is defined to be the zero angle projection.

Figure 7:
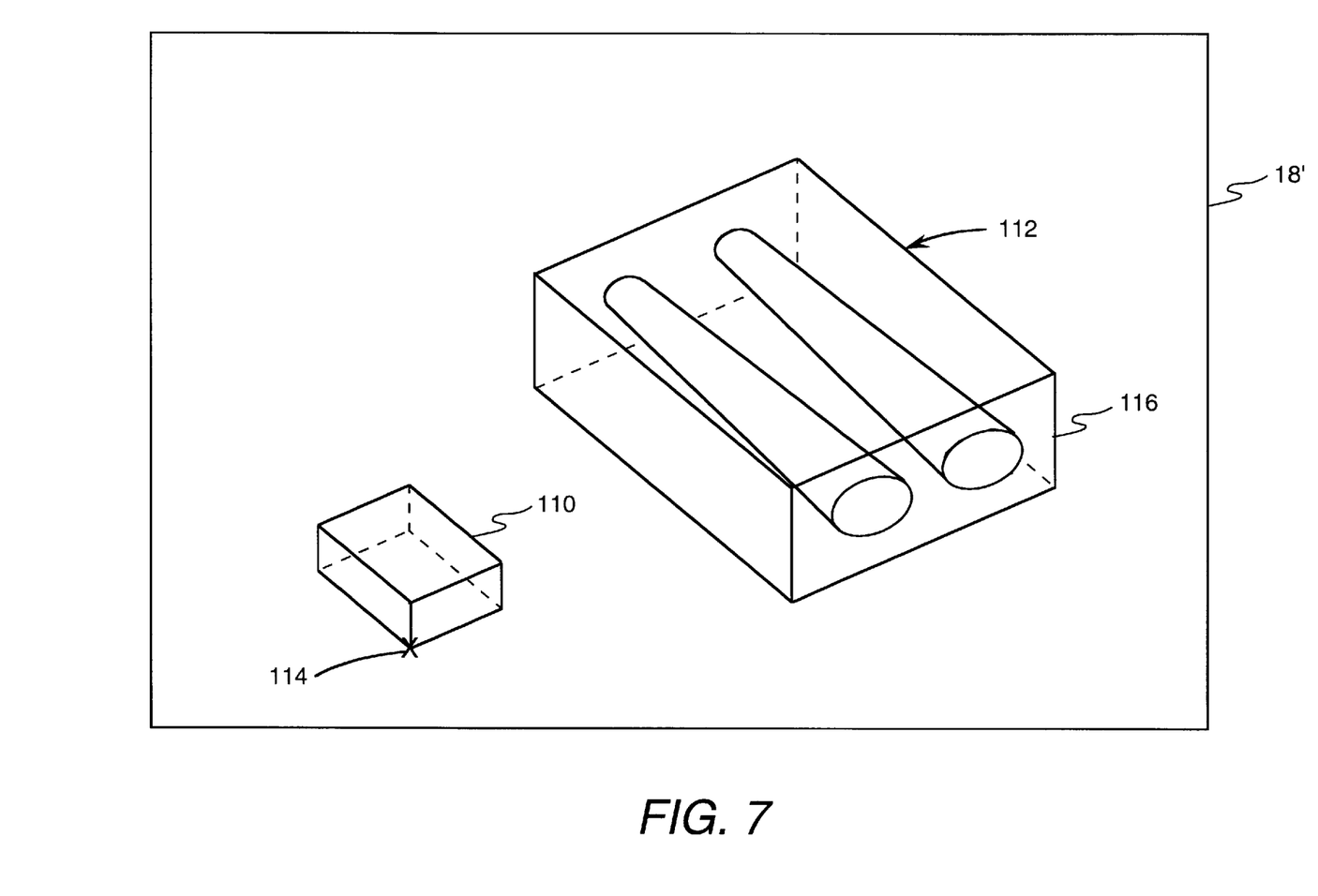
FIG. 7 is a diagram depicting a display of a projected ultrasound image made at an arbitrary angle with graphics indicating the orientation of the data volume.

In the "volume rotate" mode, the operator can use the track-ball to rotate the orientation box about the X and Y axes. Rotation about the Z axis is performed using a separate rotary knob on the operator interface. The orientation box follows the movement of the track-ball and rotary knob in "real-time" so that the user can orient the box as desired (step 70). The rotational position of each axis is shown on the display panel. When the position is set, the user depresses the "calculate" key (step 72), which causes the system to display a new projection of the three-dimensional data set (step 68) at the orientation indicated by the orientation box. FIG. 7 shows an exemplary projection 112 at an arbitrary angle indicated by the orientation box 110. The orientation box has a marker 114 in the lower front left corner while the back corners of the box are dashed to aid the user in distinguishing the front and back of the box. As an aid to visualization, a box 116 is overlaid on the projection 112 which matches the orientation box 110 and is depth shaded to appear to become darker as the box goes towards the "back" of the data volume. The user may reposition the orientation box 110 with the track-ball and rotary knobs and re-project as many times as desired. In addition, rotations of plus or minus 90° may be made with special keys on the operator interface.

In accordance with one preferred embodiment of the present invention, the rendering of a three-dimensional ultrasound data set is accomplished utilizing an object-order volume visualization technique where each voxel is mapped from the data space to the image space according to a projection matrix. The goal of this rendering method is to efficiently generate two-dimensional images from the three-dimensional data while minimizing artifacts.

Figure 8:
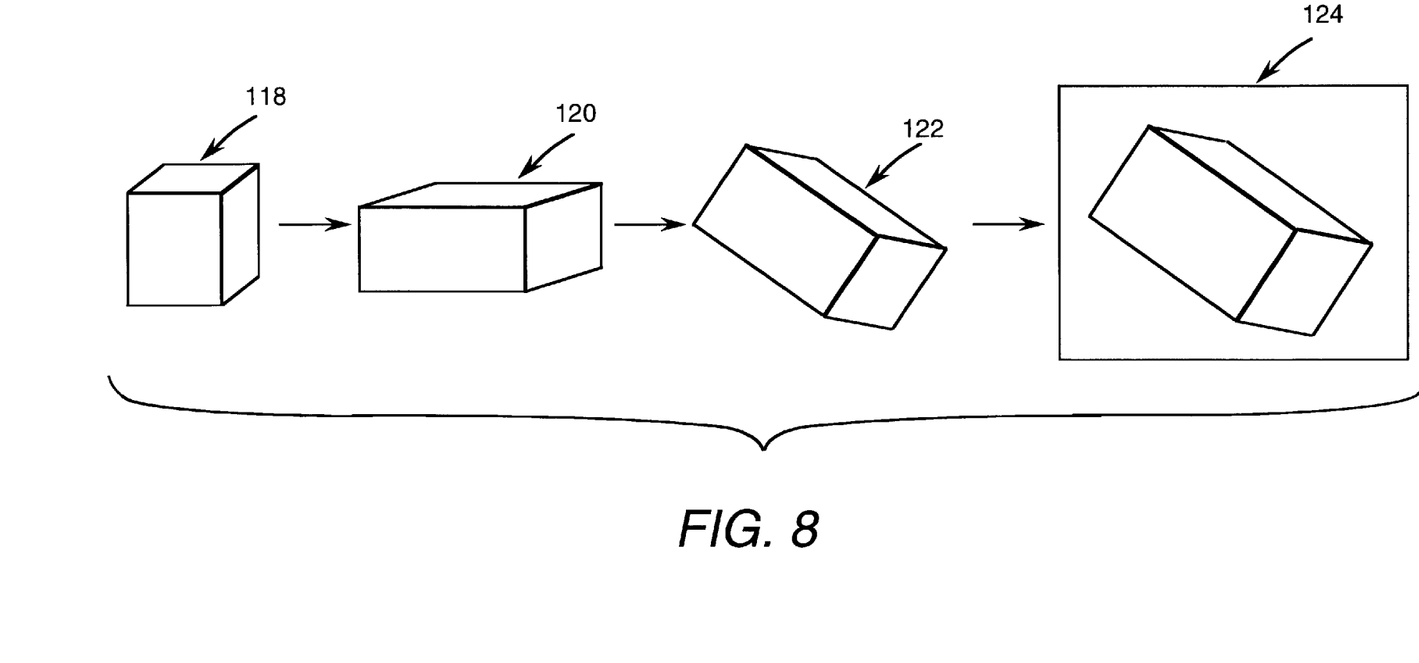
FIG. 8 is a diagram depicting a projection transform procedure in accordance with a preferred embodiment of the invention.

The data volume consists of $N_x$ by $N_y$ by $N_z$ data samples, known as voxels, along the X, Y, and Z axes respectively. In the data coordinate system, voxels are assumed to be uniformly spaced one unit apart along each axis, with the origin at the center of the data volume. Since voxels in the actual data volume may not be uniformly spaced, a scaling matrix $[S_A]$ is used to account for the aspect ratio of data samples. The data samples may then be rotated by the desired angles about the X, Y, and Z axes, and projected onto the image plane using an orthographic transformation. This process can be written as:

$$[X_d, Y_d, Z_d][S_A][R] = [x_i, y_i, z_i]$$

where $[X_d, Y_d, Z_d]$ is the coordinate of a voxel in data space, $[R]$ is the desired rotation matrix and $[x_i, y_i, z_i]$ is the image space pixel. The projection transformation $[S_A][R]$ maps $Z^3$ to $R^3$ (where the coordinates in R space are real numbers and the coordinates in Z space are integers). The z component is discarded and a floor operation (i.e., the real numbers are truncated to integers) is applied to convert $R^2$ to $Z^2$. As this projection transformation is performed, the voxel data is processed in accordance with the selected projection technique. For example, if a maximum pixel projection technique is used, each image space pixel will store only the maximum of the set of voxel data mapped to that image space pixel by the above-described projection transformation. This process is illustrated in FIG. 8, which shows the voxel data 118 being multiplied by aspect scaling (step 120), rotated by the desired angle (step 122) and projected onto the image plane (step 124).

Using the process illustrated in FIG. 8, adjacent data samples do not necessarily project to adjacent pixels on the image plane, leading to blank spots or "holes" in the projected images. To eliminate these holes, two additional scaling steps are introduced into the projection, yielding:

$$[X_d, Y_d, Z_d][S_A][R][S_H][S_H^{-1}] = [x_i, y_i, z_i]$$

This projection process is then decomposed into two steps:

$$[X_d, Y_d, Z_d][S_A][R][S_H] = [X_t, Y_t, Z_t]$$

$$[X_t', Y_t'][S_H^{-1}] = [X_i, Y_i]$$

In the first step, the data coordinate $[X_d, Y_d, Z_d]$ in $Z^3$ is mapped to the intermediate coordinate $[X_t, Y_t, Z_t]$ in $R^3$. The z component is discarded and a floor operation is used to obtain $[X_t', Y_t']$ in $Z^2$. In the second step, the inverse scaling operation is performed in two-dimensional image space.

In order to eliminate holes from the image, the scaling matrix $[S_H]$ must ensure that neighboring data samples (those that are at most one sample apart along the X, Y and Z axes in the data space) map to neighboring pixels. There are two factors that contribute to holes in the image. The first is attributable to the scaling of the sample points to account for the aspect ratio and the second is due to the rotation of the data samples. The scaling matrix $[S_H]$ eliminates the holes by scaling along the X and Y axes of the image.

The scaling factors to account for the aspect ratio are computed using the following equations:

$$X_{as} = 1.0/\|[1,0,0][R^{-1}][S_A^{-1}]\|$$

$$Y_{as} = 1.0/\|[0,1,0][R^{-1}][S_A^{-1}]\|$$

$$Z_{as} = 1.0$$

These scaling factors are used to define an intermediate scaling matrix $[S_H']$ which is used to compute the rotation scaling factors.

The scaling factors to correct for rotation are determined by projecting each of the four diagonal vectors in a cube, $V = \{[1,1,1], [-1,1,1], [-1,1,-1], [1,1,-1]\}$, onto the image plane and computing the maximum separation distance along the X and Y dimensions independently:

$$X_{rs} = 1.0/(MAX\{\|[1,0,0] \cdot [[V_i][S_A][R][S_H']]\|\} \forall V_i \in V)$$

$$Y_{rs} = 1.0/(MAX\{\|[0,1,0] \cdot [[V_i][S_A][r][S_H']]\|\} \forall V_i \in V)$$

The final scaling factors used to compute $[S_H]$ are the product of the aspect and rotation scaling factors:

$$X_s = X_{as}X_{rs}, \, Y_s = Y_{as}Y_{rs}, \, Z_s = 1.0$$

These combined scaling factors are used to ensure that voxels which are one unit apart along the X, Y and Z axes in data space are mapped onto pixels that are at most one unit apart along the X and Y axes on the image plane.

Figure 9:
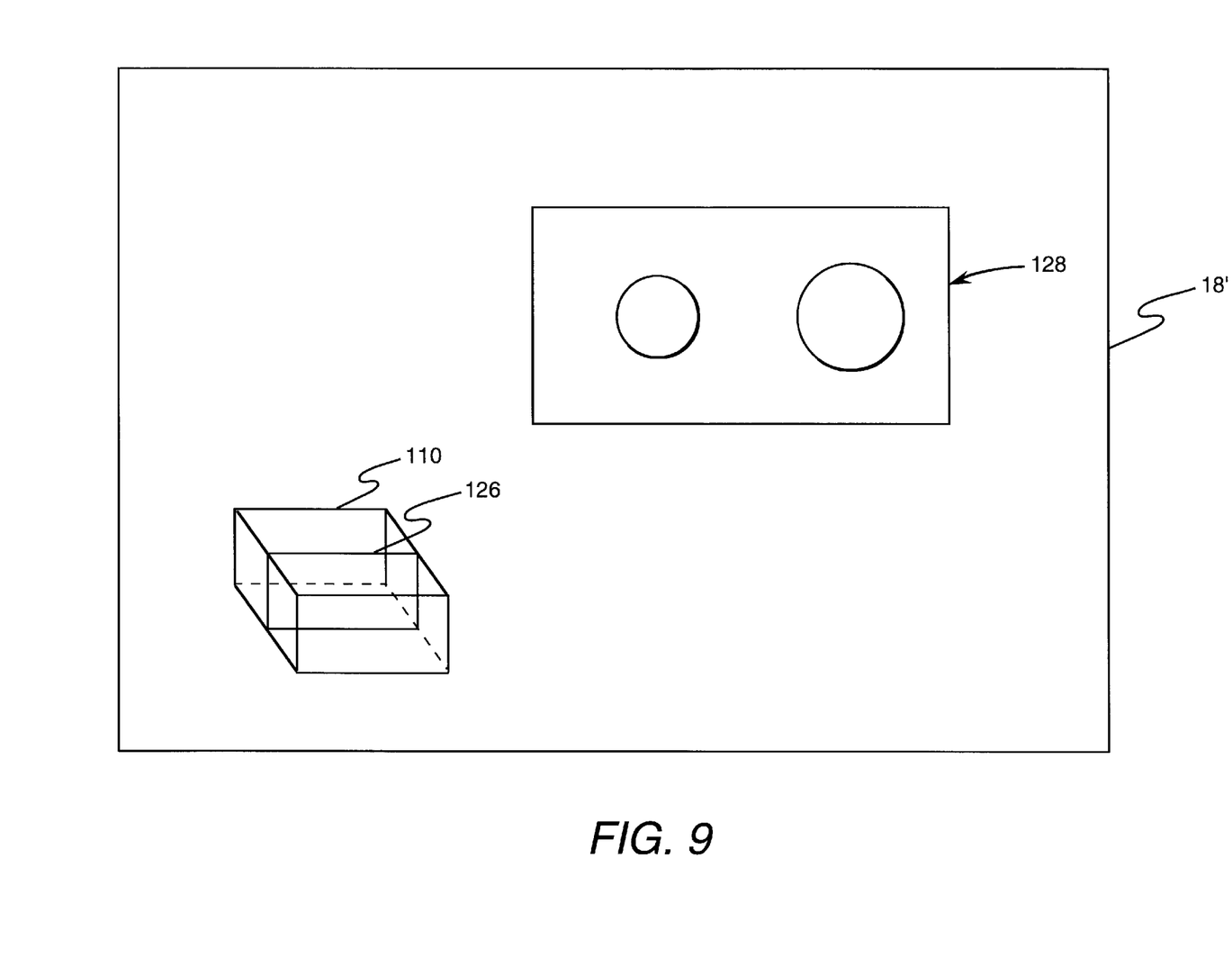
FIG. 9 is a diagram depicting a display of a two-dimensional slice with graphics representing the position and orientation of the slice relative to the data volume.

If the ultrasound imaging system operator desires to see two-dimensional slices through the data volume at the current X, Y, Z rotation orientation, the operator presses the "display mode'" key (step 74 in FIG. 5) to change from the "volume rotate" mode to the "cut-plane" (reformat) mode. Referring to FIG. 9, the orientation box 110 changes color (e.g., from green to white) and a colored (e.g., green) polygon 126 appears within the orientation box (step 76) at the center of the data volume. The green color signifies that this portion within the box can be moved. The system then produces an initial representation 128 of a two-dimensional slice through the center of the data set at the current orientation (step 78).

The shape of the slice 128 matches the shape of the green polygon 126 in the orientation box 110. The operator may then use the track-ball to scroll through the data set, displaying successive two-dimensional slices of the data set at the selected orientation and position. As the track-ball is moved (step 80), the green polygon in the orientation box moves (step 82) to visually indicate the location of the slice within the data volume and a display panel is updated to show the location of the slice as a percentage of the total volume (i.e., 50% would be the center of the data volume). When the track-ball stops moving, the system checks the status of the "display mode" key (step 84). If the "display mode" key is not depressed, the display is reformatted by the host computer to show the slice through the data volume at the last slice position when the track-ball stopped moving. If the "display mode" key is depressed, the system exits the "cut plane" mode and enters the "cut plane rotate" mode.

In the "cut plane rotate" mode, the green polygon that indicates the location of the slice through the data volume turns white and the orientation box turns green (step 86), indicating that the slice is now fixed and the data volume may rotate relative to the slice. The system then displays the reformatted slice in the manner previously described (step 88). The user may now rotate the orientation box to a new X, Y, Z orientation by moving the track-ball (step 90). As the user does so, the white polygon changes shape to show the shape of the slice. When the orientation is set, the user depresses the "calculate" key (step 92), which causes the system to display a new two-dimensional slice taken at the angle indicated by the angle of the polygon relative to the orientation box. If the "display mode" key is not depressed (step 94), the operator can reorient the data volume. If the "display mode" key is depressed, the system returns to the "volume rotate" mode.

Algorithms for producing three-dimensional projections of two-dimensional data are well known, as are techniques for reformatting data to produce arbitrary slices through a data set. The projected or reformatted data is output by the host computer to the XY display memory 26 (see FIG. 2). The image frame of projected or reformatted data is then sent to the video processor 14 and captured by the cine memory 16. The video processor superimposes the orientation box and other graphical symbols onto the image frame of projected reformatted data for output to the display monitor.

The foregoing preferred embodiments have been disclosed for the purpose of illustration. Variations and modifications of the basic concept of the invention will be readily apparent to persons skilled in the art. For example, graphical symbols other than parallelograms can be used to depict a data volume and graphical symbols other than polygons can be used to depict a slice through a data volume. Nor is the user interface limited to the specific input devices (i.e., track-ball, rocker switch, rotary switch, and keys) disclosed herein. A mouse, a joystick, a lever, a slider or other input device could also be used. All such variations and modifications are intended to be encompassed by the claims set forth hereinafter.

We claim:

1. A system for imaging of an object volume, comprising:

an ultrasound transducer array for transmitting ultrasound beams and detecting ultrasound echoes reflected from said object volume at a multiplicity of sample volumes in a scan plane;

means coupled to said ultrasound transducer array for acquiring imaging data derived from ultrasound echoes reflected from each one of a multiplicity of scan planes through said object volume;

means for storing data for each of a multiplicity of image frames corresponding to said multiplicity of scan planes;

operator interface means for receiving operator inputs;

means for defining a data volume from said multiplicity of image frames based on operator inputs;

first mode means for enabling selection of an orientation of said data volume for three-dimensional imaging in a first mode based on operator inputs;

means for generating first imaging data representing a three-dimensional projection of said data volume having said orientation onto an imaging plane by applying a projection transformation to said data volume;

means for generating first graphical data indicative of said definition and said orientation of said data volume;

a display monitor; and a video processor for concurrently displaying said three-dimensional projection and said graphical data on said display monitor in said first mode.

2. The system as defined in claim 1, further comprising:

second mode means for enabling selection of a position of a two-dimensional slice relative to said data volume having said orientation in a second mode based on operator inputs;

means for generating second imaging data representing said two-dimensional slice having said position by reformatting said data volume; and means for generating second graphical data indicative of said position of said two-dimensional slice, wherein said video processor displays said first and second graphical data and said two-dimensional slice on said display monitor concurrently in said second mode.

3. The system as defined in claim 2, wherein said first graphical data represent a box and said second graphical data represent a polygon set within said box.

4. The system as defined in claim 2, wherein said second graphical data generating means comprise means for displacing said second graphical data relative to said first graphical data on said display monitor in said second mode in response to a first operator input.

5. The system as defined in claim 4, wherein said second imaging data generating means generates second imaging data representing a two-dimensional slice having a position corresponding to a position of said second graphical data relative to said first graphical data in said second mode after said first operator input.

6. The system as defined in claim 2, further comprising third mode means for enabling selection of an orientation of said data volume relative to an axis in a third mode in response to operator input, wherein said first graphical data generating means comprise means for rotating said first graphical data relative to said second graphical data on said display monitor in said third mode in response to a first operator input.

7. The system as defined in claim 6, wherein said second imaging data generating means generates second imaging data representing a two-dimensional slice having a position corresponding to a position of said second graphical data relative to said first graphical data in said third mode in response to a second operator input.

8. The system as defined in claim 1, wherein said data volume comprises a multiplicity of voxels having respective coordinates, and said projection transformation comprises applying a scaling matrix and a rotation matrix to said coordinates of said voxels to produce coordinates of pixels in said imaging plane and applying a projection technique to said voxels for each pixel in said imaging plane.

9. The system as defined in claim 8, wherein said projection transformation further comprises applying scaling factors which ensure that voxels which are one unit apart in said data volume are mapped onto pixels that are at most one unit apart on said imaging plane.

10. The system as defined in claim 7, wherein operator interface means comprises a mode key, and said system cycles into said first, second and third modes in response to successive manipulations of said mode key.

11. A system for imaging of an object volume, comprising:

an ultrasound transducer array for transmitting ultrasound beams and detecting ultrasound echoes reflected from said object volume at a multiplicity of sample volumes in a scan plane;

means coupled to said ultrasound transducer array for acquiring a data volume derived from ultrasound echoes reflected a multiplicity of scan planes through said object volume, said data volume comprising a multiplicity of voxels having respective coordinates;

means for enabling selection of an orientation of said data volume for three-dimensional imaging;

means for generating imaging data representing a three-dimensional projection of said data volume having said orientation onto an imaging plane by applying a projection transformation to said data volume, wherein said projection transformation comprises applying a scaling matrix and a rotation matrix to said coordinates of said voxels to produce coordinates of pixels in said imaging plane and applying a projection technique to said voxels for each pixel in said imaging plane;

a display monitor; and a video processor for displaying said three-dimensional projection on said display monitor.

12. The system as defined in claim 11, wherein said projection transformation further comprises application of scaling factors which ensure that voxels which are one unit apart in said data volume are mapped onto pixels that are at most one unit apart on said imaging plane.

13. A method for imaging an object volume, comprising the steps of:

scanning an ultrasound scanner across an object;

operating the ultrasound scanner to transmit ultrasound beams and detect ultrasound echoes reflected from a multiplicity of scan planes through said object volume;

acquiring a data volume derived from ultrasound echoes reflected from said multiplicity of scan planes through said object volume;

selecting an orientation of said data volume for three-dimensional imaging in a first mode;

generating first imaging data representing a three-dimensional projection of said data volume having said orientation onto an imaging plane by applying a projection transformation to said data volume;

generating first graphical data indicative of said definition and said orientation of said data volume; and concurrently displaying said three-dimensional projection and said graphical data in said first mode.

14. The method as defined in claim 13, further comprising the steps of:

selecting a position of a two-dimensional slice relative to said data volume having said orientation in a second mode;

generating second imaging data representing said two-dimensional slice having said position by reformatting said data volume;

generating second graphical data indicative of said position of said two-dimensional slice; and concurrently displaying said first and second graphical data and said two-dimensional slice in said second mode.

15. The method as defined in claim 14, wherein said first graphical data represent a box and said second graphical data represent a polygon set within said box.

16. The method as defined in claim 14, wherein said selecting step comprises manipulating an operator input device, further comprising the step of displacing said second graphical data relative to said first graphical data on said display monitor in response to said manipulation of said operator input device in said second mode.

17. The method as defined in claim 16, further comprising the steps of:

ceasing manipulation of said operator input device; and generating a two-dimensional slice having a position corresponding to a position of said second graphical data relative to said first graphical data following cessation of manipulation of said operator input device in said second mode.

18. The method as defined in claim 14, further comprising the steps of:

selecting a third mode for enabling orientation of said data volume relative to an axis;

manipulating a first operator input device; and rotating said first graphical data relative to said second graphical data in response to manipulation of said first operator input device in said third mode.

19. The method as defined in claim 18, further comprising the steps of:

manipulating a second operator input device; and generating second imaging data representing a two-dimensional slice having a position corresponding to a position of said second graphical data relative to said first graphical data in response to manipulation of said second operator input device in said third mode.

20. The method as defined in claim 13, wherein said data volume comprises a multiplicity of voxels having respective coordinates, and said projection transformation comprises applying a scaling matrix and a rotation matrix to said coordinates of said voxels to produce coordinates of pixels in said imaging plane and applying a projection technique to said voxels for each pixel in said imaging plane.

* * * * *